United States Patent
Suzuki et al.

(10) Patent No.: US 9,261,480 B2
(45) Date of Patent: Feb. 16, 2016

(54) CERAMIC HEATER AND GAS SENSOR

(71) Applicant: NGK SPARK PLUG CO., LTD., Nagoya-shi, Aichi (JP)

(72) Inventors: Masahito Suzuki, Seki (JP); Tomohiro Kuwayama, Kasugai (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 434 days.

(21) Appl. No.: 13/915,027

(22) Filed: Jun. 11, 2013

(65) Prior Publication Data
US 2013/0327123 A1 Dec. 12, 2013

(30) Foreign Application Priority Data
Jun. 12, 2012 (JP) .................. 2012-132510

(51) Int. Cl.
*G01N 27/403* (2006.01)
*G01N 27/407* (2006.01)
*H05B 3/02* (2006.01)
*H05B 3/34* (2006.01)
*H05B 3/46* (2006.01)

(52) U.S. Cl.
CPC ............ *G01N 27/4077* (2013.01); *H05B 3/02* (2013.01); *H05B 3/34* (2013.01); *H05B 3/46* (2013.01); *H05B 2203/003* (2013.01); *H05B 2203/014* (2013.01)

(58) Field of Classification Search
CPC ................................... G01N 27/4077
See application file for complete search history.

(56) References Cited

U.S. PATENT DOCUMENTS

| 8,362,400 | B2 | 1/2013 | Sakurai et al. |
| 2001/0042746 | A1* | 11/2001 | Tanaka ............... H05B 3/48 219/541 |
| 2010/0101950 | A1 | 4/2010 | Sakurai et al. |

FOREIGN PATENT DOCUMENTS

| JP | 2010-120840 A | 6/2010 |
| JP | 2011-247657 A | 12/2011 |

* cited by examiner

*Primary Examiner* — Laura Martin
*Assistant Examiner* — Alex Devito
(74) *Attorney, Agent, or Firm* — Sughrue Mion, PLLC (57) ABSTRACT

A terminal connection portion has a plate shape extending in an axial direction and has a constant width dimension. A terminal front end edge thereof has a convex shape at a front end side in the axial direction and has a circular-arc shape with a radius from 0.5 times to 0.8 times the width dimension, and is arranged in the center between a first pad side edge and a second pad side edge, on an electrode pad. A brazing material portion has a form spreading to a front end side in the axial direction away from the terminal connection portion. A brazing material front end edge which is a front end edge of the brazing material portion has a convex and circular-arc shape at the front end side in the axial direction, and is configured to be apart from a pad front end edge.

6 Claims, 8 Drawing Sheets

CERAMIC HEATER AND GAS SENSOR

BACKGROUND OF THE INVENTION

1. Field of the Invention

The present invention relates to a ceramic heater and a gas sensor including the same.

2. Description of the Related Art

A gas sensor has been known which is attached to an exhaust pipe of vehicles, for example, and detects specific gas components contained in a detected gas such as an exhaust gas. A specific form of the gas sensor, for example, includes a detecting element detecting specific gas components in the detected gas and extending in an axial direction, and a ceramic heater heating the detecting element (for example, refer to JP-A-2010-120840).

In JP-A-2010-120840 and JP-A-2011-247657, the ceramic heater has a bar shape extending in an axial direction and includes a ceramic base body having a heater element in its interior, an electrode pad disposed on a surface of the ceramic base body and conductive with the heater element, a heater terminal member electrically connected to an external circuit, and a brazing material portion (bonding portion) bonding a terminal connection portion of the heater terminal member and the electrode pad.

In addition, in JP-A-2010-120840 and JP-A-2011-247657, the gas sensor includes an inner terminal member (contact terminal member) which is electrically connected to an inner electrode disposed in the detecting element and has a negative potential relative to the electrode pad. The contact terminal member contacts and holds the ceramic base body at a front end side thereof in the axial direction away from the electrode pad.

3. Problems to be Solved by the Invention

In the gas sensor disclosed in JP-A-2010-120840, the brazing material portion reaches the front end edge of the electrode pad. Thus, if atmospheric moisture deposits on the surface of the brazing material portion and the ceramic base body, migration may occur on the surface of the ceramic base body. In this case, metal contained in the brazing material is caused to move from the brazing material portion to the contact terminal member (portion coming into contact with the ceramic base body). As a result, a short circuit may arise between the brazing material portion and the contact terminal member.

In addition, in the gas sensor disclosed in JP-A-2011-247657, the terminal connection portion of the heater terminal member has a plate shape extending in the axial direction having a constant width dimension, and the front end edge thereof (front end edge of the terminal) has a linear shape (straight line orthogonal to the axis). In the case of using the terminal connection portion having this form, in a step of bonding the electrode pad and the terminal connection portion using the brazing material, the brazing material is wetly spread from the front end edge of the terminal to the front end side in the axial direction. However, a degree of wet spreading at one side is sometimes larger than at the other side, between a first pad side edge of the electrode pad (one of two pad side edges extending parallel to the axial direction) and a second pad side edge (the other of the above-described pad side edges). Consequently, the brazing material is likely to reach the front end edge of the electrode pad at one side. Therefore, as described above, migration may occur in which metal contained in the brazing material is caused to move and thereby a short circuit may arise between the brazing material portion and the contact terminal member.

In particular, when using a brazing material containing Ag, migration is likely to occur between the brazing material portion and the contact terminal member.

SUMMARY OF THE INVENTION

The present invention has been made in view of the above circumstances, and an object thereof is to provide a ceramic heater and a gas sensor including the same, in which migration of Ag is unlikely to occur between a brazing material portion and a contact terminal member.

The above object of the present invention has been achieved by providing (1) a gas sensor having an axis, a rear end side and a front end side, the gas sensor including a ceramic heater and a contact terminal member, the ceramic heater comprising: a ceramic base body having a bar shape extending in the axial direction and a heater element disposed inside the ceramic base body; an electrode pad disposed on a surface of a base end side in the axial direction of the ceramic base body and conductive with the heater element, the electrode pad having a first pad side edge and a second pad side edge extending parallel to the axial direction, and a pad front end edge located at a front end side in the axial direction with respect to the first and second pad side edges and connecting a front end of the first pad side edge and a front end of the second pad side edge; a heater terminal member having a terminal connection portion arranged at the base end side in the axial direction apart from the pad front end edge; and a brazing material portion formed of a brazing material containing Ag, arranged on the electrode pad and interposed between the electrode pad and the terminal connection portion to bond the electrode pad and the terminal connection portion; and the contact terminal member having a negative potential relative to the electrode pad and coming into contact with the ceramic base body at the front end side in the axial direction apart from the pad front end edge. The terminal connection portion has a plate shape extending in the axial direction having a constant width dimension, and a terminal front end edge thereof has a convex shape at the front end side in the axial direction and has a circular-arc shape with a radius from 0.5 times to 0.8 times the width dimension, which terminal connection portion is arranged in the center between the first pad side edge and the second pad side edge, on the electrode pad. The brazing material portion has a form spreading to the front end side in the axial direction away from the terminal connection portion. A brazing material front end edge which is a front end edge of the brazing material portion has a convex and circular-arc shape at the front end side in the axial direction, and is configured to be apart from the pad front end edge.

In the above-described gas sensor (1), the front end edge (front end side edge in the axial direction) of the brazing material portion containing Ag has a convex and circular-arc shape at the front end side in the axial direction and is apart from the pad front end edge. Accordingly, Ag migration is unlikely to occur between the brazing material portion and the contact terminal member.

In the gas sensor (1), the brazing material front end edge (front end edge of the brazing material portion) having the above-described form is made in the following manner.

More specifically, the terminal connection portion has a plate shape extending in the axial direction with a constant width dimension, and the terminal front end edge thereof has a convex shape at the front end side in the axial direction and a circular-arc shape with a radius from 0.5 times to 0.8 times the width dimension. Furthermore, the terminal connection portion is arranged at the center between the first pad side edge and the second pad side edge, on the electrode pad.

In this manner, when bonding the electrode pad and the terminal connection portion with the brazing material, the brazing material is wetly spread substantially uniformly to the left and right in a circular-arc shape from the terminal front end edge to the front end side in the axial direction. That is, it is possible to have the same degree of wet spreading of the brazing material in both the first pad side edge side of the electrode pad and the second pad side edge side of the electrode pad. Accordingly, it is possible to prevent the brazing material from reaching the front end edge of the electrode pad at one side due to the degree of wet spreading in one side that is larger than that of the other side between the first pad side edge side and the second pad side edge side. Thus, with regard to the brazing material portion, the front end edge thereof can have a convex and circular-arc shape at the front end side in the axial direction apart from the pad front end edge.

In some cases, the form of the pad front end edge is configured to include a front end side orthogonal to the axial line in a plane view (in other words, a front end side located on a plane orthogonal to the axis), a first corner portion with a circular-arc shape connecting one end of the front end side and the front end of the first pad side edge, and a second corner portion with a circular-arc shape connecting the other end of the front end side and the front end of the second pad side edge. In the case of the pad front end edge having such a form, an electric field tends to concentrate on the first corner portion and the second corner portion. Accordingly, in particular, Ag migration is likely to occur in the first corner portion and the second corner portion.

In contrast, in the gas sensor (1) described above, the brazing material has a convex and circular-arc shape at the front end side in the axial direction. Accordingly, the brazing material front end edge can be separated far from the first corner portion and the second corner portion. Therefore, Ag migration is unlikely to occur between the brazing material portion and the contact terminal member.

In a preferred embodiment (2) of the gas sensor (1), the terminal connection portion is arranged on the electrode pad, at a position spaced with a distance longer than 6.6 times the plate thickness of the terminal connection portion from the pad front end edge to the base end side in the axial direction.

When bonding (brazing) the terminal connection portion to the electrode pad using the brazing material, a portion of the melted brazing material is wetly spread from the front end of the terminal connection portion to the front end side in the axial direction. The distance of the wet spreading depends on the plate thickness of the terminal connection portion. The investigation of the present inventors has revealed that the distance of the wet spreading of the brazing material from the front end of the terminal connection portion to the front end side in the axial direction is approximately 6.6 times the plate thickness of the terminal connection portion. Therefore, if the terminal connection portion is arranged to be spaced with a distance longer than 6.6 times the plate thickness of the terminal connection portion from the pad front end edge to the base end side in the axial direction, it is possible to inhibit the brazing material (brazing material portion) from being wetly spread up to the front end edge of the electrode pad (i.e., from reaching the pad front end edge). In this manner, the gas sensor (2) is formed such that the front end edge of the brazing material portion (brazing material front end edge) is apart from the pad front end edge.

In another preferred embodiment (3) of the gas sensor according to (1) or (2) above, a plated layer covers the brazing material portion and is formed of a metal selected from the group consisting of nickel, chromium and gold.

If the brazing material portion is covered by any one of layers among a nickel plated layer, a chromium plated layer and a gold plated layer, it is possible to prevent corrosion of the brazing material portion. In addition, the above-described migration is even more unlikely to occur.

In a second aspect, the present invention provides (4) a ceramic heater having an axis, a rear end side and a front end side, the ceramic heater comprising: a ceramic base body having a bar shape extending in the axial direction and a heater element disposed inside the ceramic base body; an electrode pad disposed on a surface of a base end side in the axial direction of the ceramic base body and conductive with the heater element, the electrode pad having a first pad side edge and a second pad side edge extending parallel to the axial direction, and a pad front end edge located at a front end side in the axial direction with respect to the first and second pad side edges and connecting a front end of the first pad side edge and a front end of the second pad side edge; a heater terminal member having a terminal connection portion arranged at the base end side in the axial direction apart from the pad front end edge; and a brazing material portion formed of a brazing material containing Ag, arranged on the electrode pad and interposed between the electrode pad and the terminal connection portion to bond the electrode pad and the terminal connection portion. The terminal connection portion has a plate shape extending in the axial direction having a constant width dimension, and a terminal front end edge thereof has a convex shape at the front end side in the axial direction and has a circular-arc shape with a radius from 0.5 times to 0.8 times the width dimension, which terminal connection portion is arranged in the center between the first pad side edge and the second pad side edge, on the electrode pad. The brazing material portion has a form spreading to the front end side in the axial direction away from the terminal connection portion, and a brazing material front end edge which is a front end edge of the brazing material portion that has a convex and circular-arc shape at the front end side in the axial direction, and configured to be apart from the pad front end edge.

In the above-described ceramic heater, the front end edge (front end side edge in the axial direction) of the brazing material portion containing Ag has a convex and circular-arc shape at the front end side in the axial direction and is set apart from the pad front end edge. Accordingly, Ag migration is unlikely to occur between the brazing material portion and the contact terminal member.

In the above-described ceramic heater, similar to the gas sensor described above, the terminal connection portion is formed in a plate shape extending in the axial direction with a constant width dimension, and the terminal front end edge thereof has a convex shape at the front end side in the axial direction and has a circular-arc shape having a radius from 0.5 times to 0.8 times the width dimension. Furthermore, the terminal connection portion is arranged in the center between the first pad side edge and the second pad side edge, on the electrode pad. In this manner, similar to the gas sensor described above, when bonding the electrode pad and the terminal connection portion using the brazing material, the front end edge of the brazing material can be formed to be apart from the pad front end edge and can have a convex and circular-arc shape at the front end side in the axial direction.

In addition, in the above-described ceramic heater, the brazing material front end edge has a convex and circular-arc shape at the front end side in the axial direction. Accordingly, similar to the gas sensor described above, the brazing material portion can be separated far from the first corner portion and the second corner portion of the pad front end edge. Therefore, Ag migration is unlikely to occur between the brazing material portion and the contact terminal member.

In a preferred embodiment (5) of the ceramic heater (4), the terminal connection portion is arranged on the electrode pad, at a position spaced with a distance longer than 6.6 times the plate thickness of the terminal connection portion from the pad front end edge to the base end side in the axial direction.

As described above, when bonding (brazing) the terminal connection portion to the electrode pad using the brazing material, the wet spreading distance of the brazing material from the front end of the terminal connection portion to the front end side in the axial direction is approximately 6.6 times the plate thickness of the terminal connection portion. Therefore, if the terminal connection portion is arranged to be spaced with a distance longer than 6.6 times the plate thickness of the terminal connection portion from the pad front end edge to the base end side in the axial direction, it is possible to inhibit the brazing material (brazing material portion) from being wetly spread up to the front end edge of the electrode pad (i.e., from reaching the pad front end edge). Thus, the above-described ceramic heater (5) is formed such that the front end edge of the brazing material portion (brazing material front end edge) is apart from the pad front end edge.

In another preferred embodiment (6) of the ceramic heater according to (4) or (5) above, a plated layer covers the brazing material portion and is formed of a metal selected from the group consisting of nickel, chromium and gold.

If the brazing material portion is covered by any one of layers among a nickel plated layer, a chromium plated layer and a gold plated layer, it is possible to prevent corrosion of the brazing material portion. In addition, the above-described migration is even more unlikely to occur.

In a third aspect (7), the present invention provides a method of manufacturing a gas sensor having an axis, a rear end side and a front end side, the gas sensor including a ceramic heater and a contact terminal member, the ceramic heater comprising: a ceramic base body having a bar shape extending in the axial direction and a heater element disposed inside the ceramic base body; an electrode pad disposed on a surface of a base end side in the axial direction of the ceramic base body and conductive with the heater element, the electrode pad having a first pad side edge and a second pad side edge extending parallel to the axial direction, and a pad front end edge located at a front end side in the axial direction with respect to the first and second pad side edges and connecting a front end of the first pad side edge and a front end of the second pad side edge; a heater terminal member having a terminal connection portion arranged at the base end side in the axial direction apart from the pad front end edge; and a brazing material portion formed of a brazing material containing Ag, arranged on the electrode pad and interposed between the electrode pad and the terminal connection portion to bond the electrode pad and the terminal connection portion, and the contact terminal member having a negative potential relative to the electrode pad and coming into contact with the ceramic base body at the front end side in the axial direction apart from the pad front end edge, in which the terminal connection portion has a plate shape extending in the axial direction having a constant width dimension. The manufacturing method includes a step of bonding the electrode pad and the terminal connection portion using the brazing material. In the bonding step, a heater terminal member is used in which the terminal front end edge of the terminal connection portion has a convex shape at the front end side in the axial direction and has a circular-arc shape with a radius from 0.5 times to 0.8 times the width dimension. The terminal connection portion is arranged in the center between the first pad side edge and the second pad side edge, on the electrode pad. Then, the melted brazing material is brought into contact with the electrode pad and the terminal connection portion so as to infiltrate between the electrode pad and the terminal connection portion, and is caused to wet spread on the electrode pad.

According to the above-described manufacturing method, in the bonding step, in a state where the terminal connection portion (having a plate shape extending in the axial direction having a constant width dimension and whose terminal front end edge has a convex shape at the front end side in the axial direction and has a circular-arc shape with a radius from 0.5 times to 0.8 times the width dimension) is arranged in the center between the first pad side edge and the second pad side edge, on the electrode pad, the melted brazing material (the brazing material containing Ag) is brought into contact with the electrode pad and the terminal connection portion so as to infiltrate between the electrode pad and the terminal connection portion, and is caused to wet spread on the electrode pad, whereby the electrode pad and the terminal connection portion are bonded using the brazing material.

In this manner, in the bonding step, the brazing material is wetly spread substantially uniformly to the left and right in a circular-arc shape from the terminal front end edge to the front end side in the axial direction. That is, it is possible to have the same degree of wet spreading of the brazing material in both the first pad side edge side of the electrode pad and the second pad side edge side of the electrode pad. Accordingly, it is possible to prevent the brazing material from reaching the front end edge of the electrode pad at one side due to a degree of wet spreading at one side that is larger than that in the other side between the first pad side edge side and the second pad side edge side. Thus, according to the above-described manufacturing method, with regard to the brazing material, the front end edge thereof can have a convex and circular-arc shape at the front end side in the axial direction and can have a form apart from the pad front end edge. Accordingly, Ag migration is unlikely to occur between the brazing material portion and the contact terminal member.

Furthermore, in the bonding step, the terminal connection portion is preferably arranged to be spaced with a distance longer than 6.6 times the plate thickness of the terminal connection portion from the pad front end edge to the base end side in the axial direction, on the electrode pad.

In the above-described manufacturing method, the terminal connection portion is arranged to be spaced with distance longer than 6.6 times the plate thickness of the terminal connection portion from the pad front end edge to the base end side in the axial direction. Accordingly, in the bonding step, the melted brazing material reliably does not wetly spread up to the front end edge of the electrode pad (i.e., cannot reach the pad front end edge). Therefore, it is possible to reliably separate the front end edge of the brazing material portion from the front end edge of the electrode pad.

In a fourth aspect (8), the present invention provides a method of manufacturing a ceramic heater having an axis, a rear end side and a front end side, the ceramic heater comprising: a ceramic base body having a bar shape extending in the axial direction and a heater element disposed inside the ceramic base body; an electrode pad disposed on a surface of a base end side in the axial direction of the ceramic base body and conductive with the heater element, the electrode pad having a first pad side edge and a second pad side edge extending parallel to the axial direction, and a pad front end edge located at a front end side in the axial direction with respect to the first and second pad side edges and connecting a front end of the first pad side edge and a front end of the second pad side edge; a heater terminal member having a terminal connection portion arranged at the base end side in the axial direction apart from the pad front end edge; and a brazing material portion formed of a brazing material containing Ag, arranged on the electrode pad and interposed between the electrode pad and the terminal connection portion to bond the electrode pad and the terminal connection portion. The terminal connection portion has a plate shape extending in the axial direction having a constant width dimension. The manufacturing method includes a bonding step of bonding the electrode pad and the terminal connection portion using the brazing material. In the bonding step, a heater terminal member is used where the terminal front end edge of the terminal connection portion has a convex shape at the front end side in the axial direction and has a circular-arc shape with a radius from 0.5 times to 0.8 times the width dimension. The terminal connection portion is arranged in the center between the first pad side edge and the second pad side edge, on the electrode pad. Then, the melted brazing material is brought into contact with the electrode pad and the terminal connection portion so as to infiltrate between the electrode pad and the terminal connection portion, and is caused to be wetly spread on the electrode pad.

According to the above-described manufacturing method, in the bonding step, in a state where the terminal connection portion (having a plate shape extending in the axial direction having a constant width dimension and whose terminal front end edge has a convex shape at the front end side in the axial direction and has a circular-arc shape with a radius from 0.5 times to 0.8 times the width dimensions) is arranged in the center between the first pad side edge and the second pad side edge, on the electrode pad, the melted brazing material (the brazing material containing Ag) is brought into contact with the electrode pad and the terminal connection portion so as to infiltrate between the electrode pad and the terminal connection portion, and is caused to wetly spread on the electrode pad, whereby the electrode pad and the terminal connection portion is bonded using the brazing material.

In this manner, in the bonding step, the brazing material is wetly spread substantially uniformly to the left and right in a circular-arc shape from the terminal front end edge to the front end side in the axial direction. Accordingly, it is possible to prevent the brazing material from reaching the front end edge of the electrode pad at one side due to a degree of wet spreading at one side that is larger than that in the other side between the first pad side edge side and the second pad side edge side. Thus, according to the above-described manufacturing method, with regard to the brazing material portion, the front end edge thereof can have a convex and circular-arc shape at the front end side in the axial direction and can have a form apart from the pad front end edge. Accordingly, Ag migration is unlikely to occur between the brazing material portion and the contact terminal member.

Furthermore, in the bonding step, the terminal connection portion is preferably arranged to be spaced with a distance longer than 6.6 times the plate thickness of the terminal connection portion from the pad front end edge to the base end side in the axial direction, on the electrode pad.

In the above-described manufacturing method, the terminal connection portion is arranged to be spaced with a distance longer than 6.6 times the plate thickness of the terminal connection portion from the pad front end edge to the base end side in the axial direction. Accordingly, in the bonding step, the melted brazing material reliably does not wetly spread up to the front end edge of the electrode pad (i.e., cannot reach the pad front end edge). Therefore, it is possible to reliably separate the front end edge of the brazing material portion from the front end edge of the electrode pad.

DETAILED DESCRIPTION OF THE PREFERRED EMBODIMENTS

Embodiment

Next, an embodiment of the present invention will be described with reference to the accompanying drawings. However, the present invention should not be construed as being limited thereto.

Figure 1:
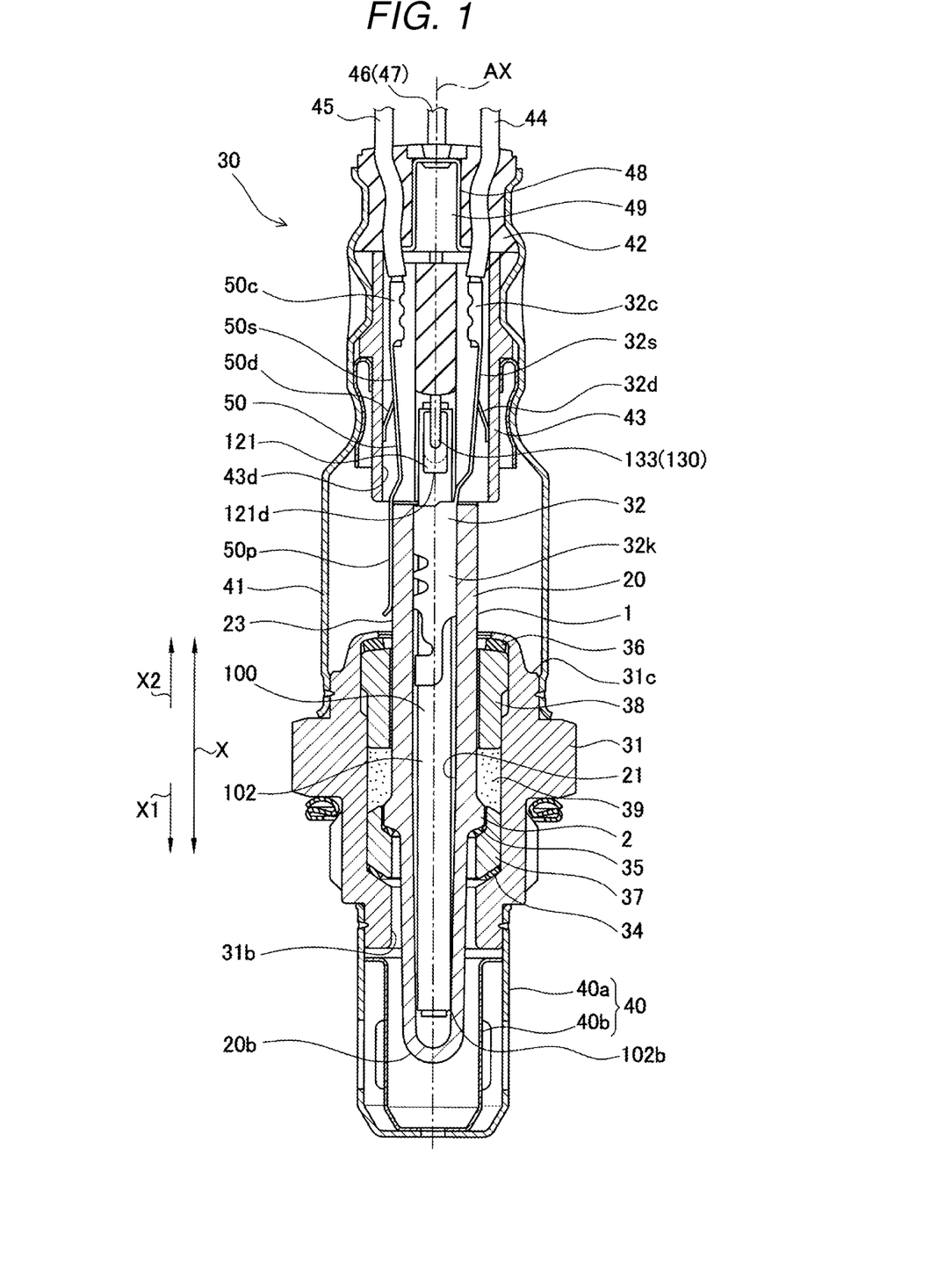
FIG. 1 is a longitudinal cross-sectional view of a gas sensor according to an embodiment of the invention.

A gas sensor 30 according to the present embodiment includes a detecting element 20 and a tubular metallic shell 31 surrounding the detecting element 20 as illustrated in FIG. 1. Furthermore, the gas sensor 30 includes an outer terminal member 50, an inner terminal member 32 and a ceramic heater 100.

The detecting element 20 has a form extending in a direction of an axial line X (direction along an axial line AX or simply "axial direction" which is the vertical direction in FIG. 1). The detecting element 20 has a base body 1 with a bottomed tubular shape, an outer electrode 23 formed on an outer surface of the base body 1 and made of a precious metal (for example, platinum), and an inner electrode 21 formed on an inner surface of the base body 1 and made of a precious metal (for example, platinum) (precious metal plated layer). The detecting element 20 detects specific gas components (e.g., oxygen component) contained in a gas to be detected (exhaust gas).

The base body 1 is made of a solid electrolyte composed mainly of zirconia, has a form extending in the axial direction, and has a bottomed tubular shape in which a front end side X1 in the axial direction (lower side in FIG. 1) is closed and a base end side X2 in the axial direction (upper side in FIG. 1) is open. An annular flange portion 2 protruding radially outward is formed in a substantially intermediate portion of the base body 1 in the axial direction. For example, the base body 1 can be fabricated such that the solid electrolyte composed mainly of zirconia is molded into a molded body with a bottomed tubular shape using a known press molding method, and then subjected to firing at a temperature of approximately 1,500° C. for approximately two hours.

The metallic shell 31 engages with and holds the flange portion 2 of the detecting element 20 (base body 1) by interposing metal packings 34, 35 and 36, insulators 37 and 38, and talc powder 39 in the hollow cylindrical interior thereof. In this manner, the detecting element 20 is held by the metallic shell 31 in a state where a front end portion 20b of the detecting element 20 protrudes from a front end side opening 31b of the metallic shell 31.

Furthermore, a protector 40 is attached to the metallic shell 31 so as to cover the front end portion 20b of the detecting element 20 protruding from the front end side opening 31b of the metallic shell 31. The protector 40 has a double structure having an outer protector 40a and an inner protector 40b. The outer protector 40a and the inner protector 40b have a plurality of vent holes for passing the exhaust gas therethrough. Therefore, it is possible to bring the exhaust gas introduced through the vent holes of the protector 40 into contact with the outer electrode 23 formed on the outer surface of the base body 1.

In addition, a front end portion of an external metal tube 41 having a tubular shape is fixedly attached to a connection portion 31c located at a rear end side (upper side in FIG. 1) of the metallic shell 31 by laser welding the entire circumference thereof from the outside. In addition, a grommet 42 made of fluorine rubber is fitted into a rear end side opening of the external metal tube 41, which is sealed by crimping. A separator 43 made of an alumina ceramic having insulation properties is disposed at a front end side (lower side in FIG. 1) of the grommet 42. Then, sensor output lead wires 44 and 45 and heater lead wires 46 and 47 are inserted into a through hole of the grommet 42 and a through hole (holding hole 43d) of the separator 43. The heater lead wires 46 and 47 are connected to a heater terminal member 130 of the ceramic heater 100.

A through hole along the axial line AX is also formed in the center of the grommet 42. A metal pipe 49 covered by a sheet-like filter 48 having both water repellency and air permeability is fitted into the through hole. In this manner, air present outside the gas sensor 30 can be introduced into the external metal tube 41 through the filter 48, and can be further introduced into the detecting element 20 so as to contact the inner electrode 21.

Figure 2:
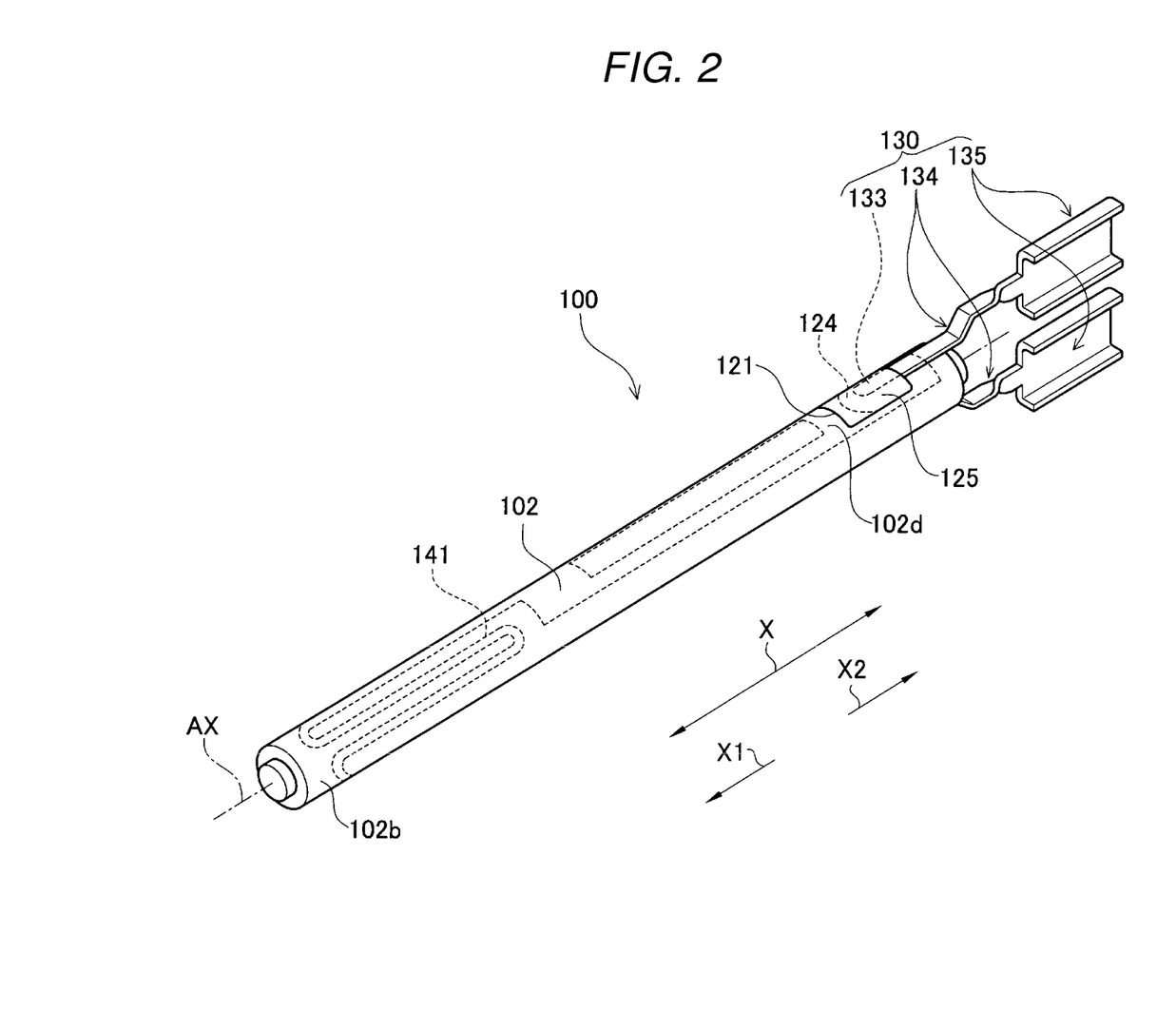
FIG. 2 is a perspective view of a ceramic heater according to an embodiment of the invention.

The ceramic heater 100 forms a bar shape (specifically, cylindrical shape) extending in the axial direction (direction along the axial line AX, vertical direction in FIG. 1). As illustrated in FIG. 2, the ceramic heater 100 has a ceramic base body 102, an electrode pad 121, a heater terminal member 130 and a brazing material portion 124. Among them, the ceramic base body 102 forms a bar shape extending in the axial direction and has a heater element 141 arranged inside of the base body 102 (refer to FIGS. 2 and 3).

Figure 5:
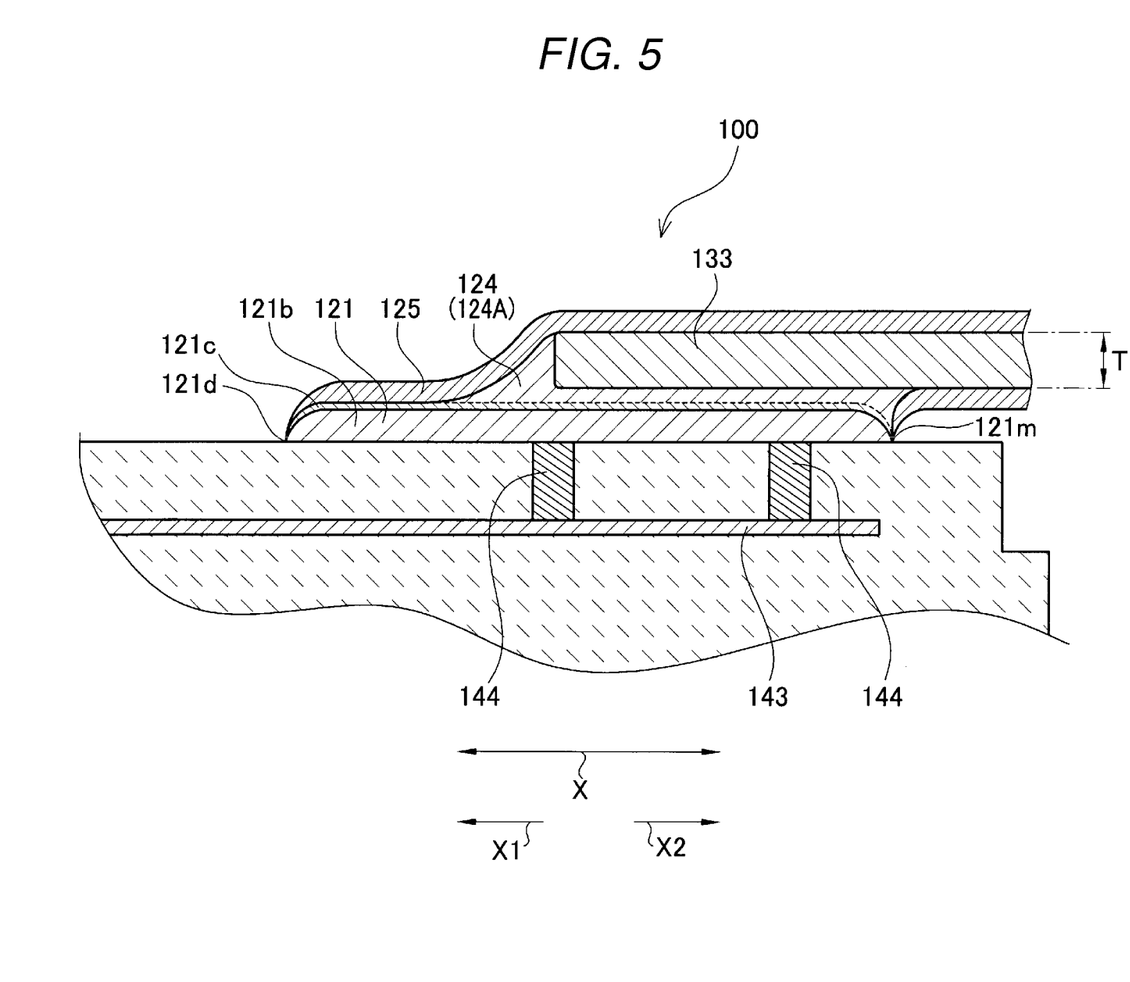
FIG. 5 is a cross-sectional view taken along the line B-B in FIG. 4.
Figure 6:
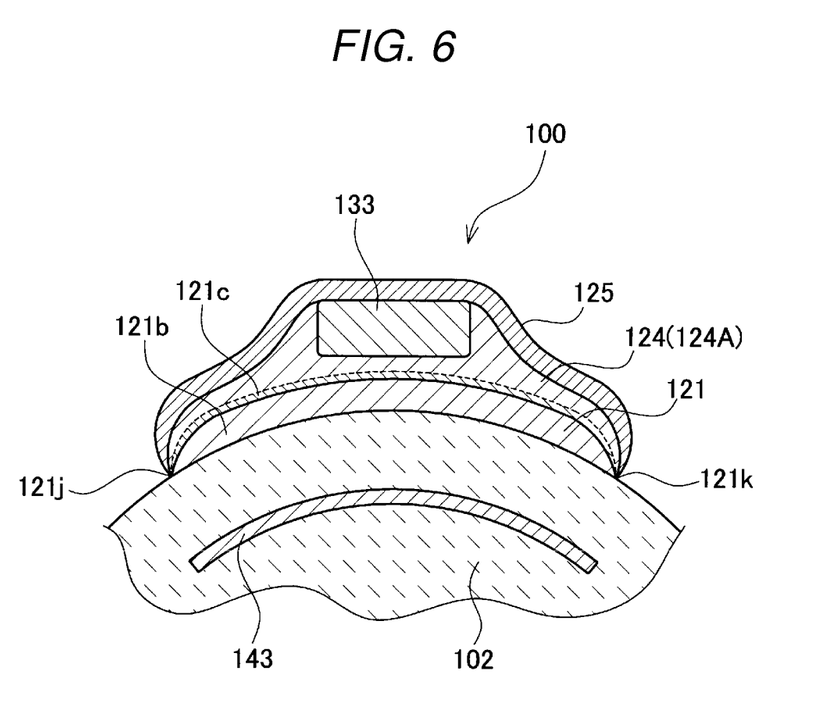
FIG. 6 is a cross-sectional view taken along the line C-C in FIG. 4.

The electrode pad 121 is formed from a pad main body portion 121b and a nickel plated layer 121c covering the pad main body portion 121b (refer to FIGS. 5 and 6). The pad main body portion 121b is a pad-shaped metal layer which includes a principal material (in the present embodiment, tungsten) consisting of at least one or more types of elements selected from tungsten and molybdenum in an amount of up to 90 wt % or more and in which the content of insulating ceramic (in the present embodiment, alumina powder) is 10 wt % or less. As the insulating ceramic contained in the pad main body portion 121b, mullite, spinel or the like can be used in addition to alumina.

In addition, a portion of the nickel plated layer 121c (portion in contact with the brazing material portion 124) is diffused into the brazing material portion 124. This is because in a bonding process (described below), the portion of the nickel plated layer 121c (portion in contact with the brazing material 124A) diffuses into a brazing material 124A (brazing material portion 124) when bonding the electrode pad 121 and a terminal connection portion 133 using the brazing material 124A.

Figure 3:
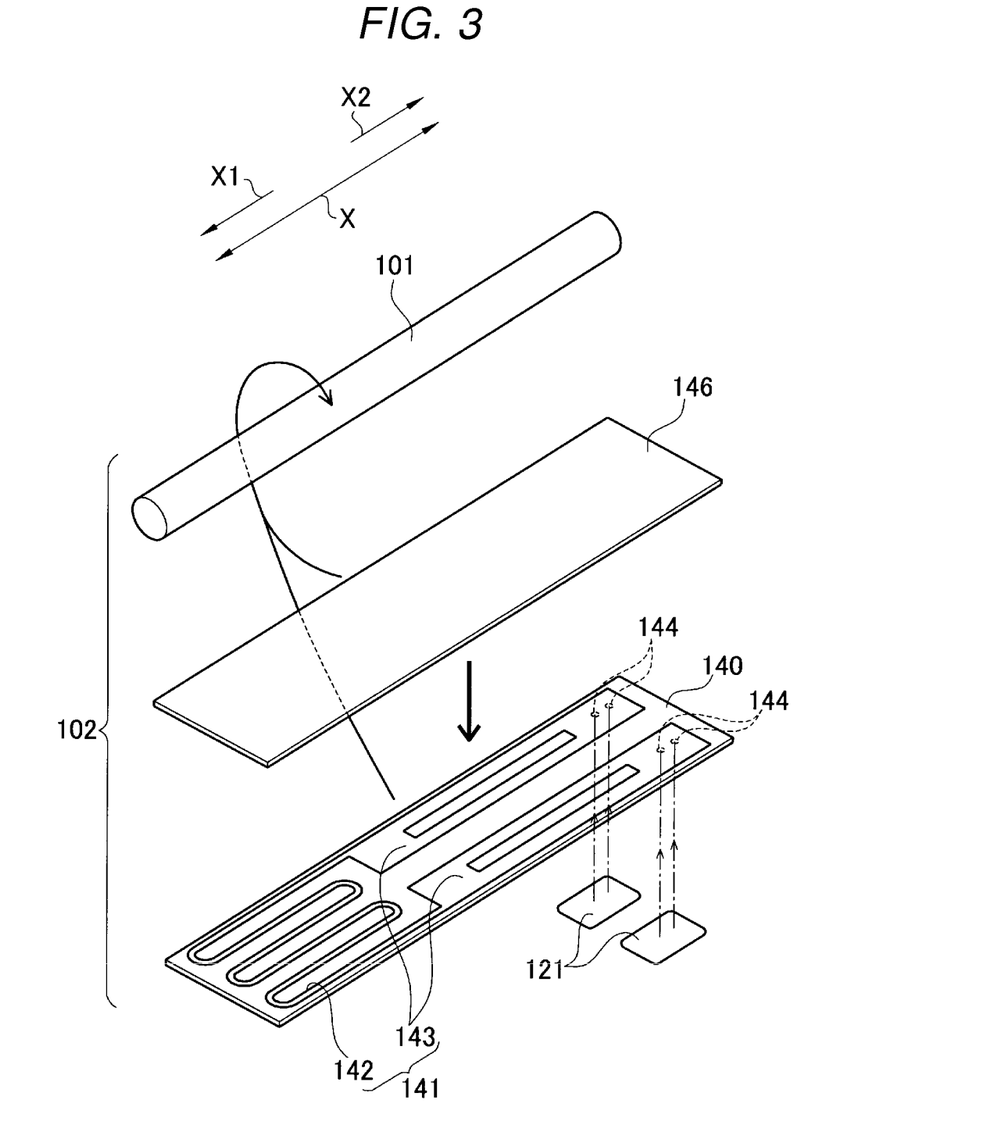
FIG. 3 is an exploded perspective view of the ceramic heater.

The electrode pad 121 is disposed on a surface 102d at the base end side X2 (upper side in FIG. 1) in the axial direction within the ceramic base body 102 and is conductive with the heater element 141 through a via 144 (filled via conductor) (refer to FIGS. 2, 3 and 5). The electrode pad 121 has a first pad side edge 121j and a second pad side edge 121k which extend parallel to the axial direction, and a pad front end edge 121d located at the front end side X1 in the axial direction with respect to the first and second pad side edges and connecting a front end 121j1 of the first pad side edge 121j and a front end 121k1 of the second pad side edge 121k (refer to FIGS. 4 and 7).

Figure 7:
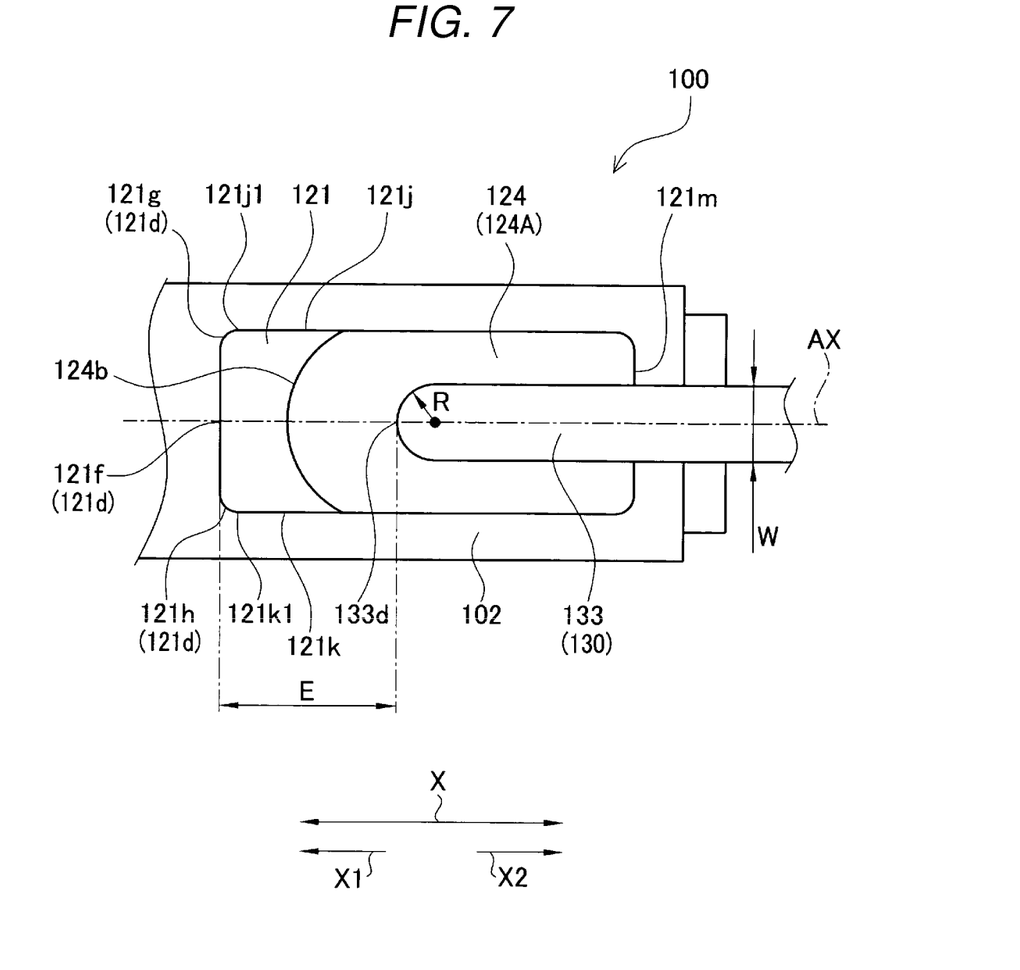
FIG. 7 is a plan view illustrating a form of a brazing material portion according to an embodiment of the invention.

The pad front end edge 121d is formed from a front end side 121f orthogonal to the axial line AX in a plane view (in other words, front end side 121f located on a plane orthogonal to the axial line AX), a first corner portion 121g with a circular-arc shape connecting one end of the front end side 121f and a front end of the first pad side edge 121j, and a second corner portion 121h with a circular-arc shape connecting the other end of the front end side 121f and a front end of the second pad side edge 121k (refer to FIG. 7). FIG. 7 corresponds to a view where a plated layer 125 is removed (seen through) in FIG. 4.

The heater terminal member 130 is electrically connected to an external circuit (not illustrated) through the heater lead wires 46 and 47. The heater terminal member 130 has a terminal connection portion 133 with a plate shape, a crimping portion 135, and a connection portion 134 connecting both of the heater terminal member 130 and the terminal connection portion 133 (refer to FIG. 2). The crimping portion 135 grips core wires of the heater lead wires 46 and 47 (refer to FIG. 1) respectively by means of crimping and is electrically connected to the heater lead wires 46 and 47.

The terminal connection portion 133 is made of nickel alloy and is arranged in the center between the first pad side edge 121j and the second pad side edge 121k, on the electrode pad 121, and at the base end side X2 (right side in FIGS. 4, 5 and 7) in the axial direction but not at the pad front end edge 121d.

The brazing material portion 124 is made of the brazing material 124A containing Ag (specifically, a brazing material containing Ag up to 72 wt % and Cu up to 28 wt %) and is arranged on the electrode pad 121. The brazing material portion 124 is interposed between the electrode pad 121 and the terminal connection portion 133 to bond the same (refer to FIGS. 5 and 6).

In the present embodiment, the brazing material portion 124 is covered with the plated layer 125. This can prevent corrosion of the brazing material portion 124. In addition, it is possible to inhibit migration (described below). The plated layer 125 is formed of any one among nickel plating, chrome plating and gold plating.

Here, the ceramic base body 102 will be described in detail. As illustrated in FIG. 3, the ceramic base body 102 is manufactured in such a manner that green sheets 140 and 146 made of alumina ceramic having a high insulation property are wound around the outer periphery of a porcelain tube 101 made of alumina ceramic with a round bar shape (cylindrical shape) and all of these are fired.

The heater element 141 (heater pattern) is formed on the green sheet 140. The heater element 141 includes a heat generation portion 142 and a pair of lead portions 143 (anode and cathode) respectively connected to both ends of the heat generation portion 142. As a material for the heater element 141, various conductive materials such as tungsten and molybdenum can be used. In a rear end side of the green sheet 140, a pair of vias 144 are formed on each of the lead portions 143. The electrode pad 121 is electrically connected to the lead portions 143 of the heater element 141 through the pair of vias 144.

The green sheet 146 is pressed against the green sheet 140 (surface on which the heater element 141 is formed). Alumina paste is applied to the surface of the green sheet 146 opposite the surface against which the green sheet 140 is pressed. A ceramic heater molded body is formed in such a manner that the green sheets 140 and 146 are wound around the porcelain tube 101 with the paste application surface being located inward and then pressed inward from the outer periphery. Thereafter, the ceramic base body 102 is formed by firing the ceramic heater molded body.

The ceramic heater 100 is arranged inside the detecting element 20 (inside the cylinder of the base body 1) and its position is held by an inner terminal member 32 (refer to FIG. 1). Specifically, the ceramic base body 102 of the ceramic heater 100 is gripped by an element insertion portion 32k of the inner terminal member 32 (contact terminal member) and is held in a state where the front end portion 102b is in contact with the inner electrode 21 of the detecting element 20. In this manner, the detecting element 20 (base body 1) can be properly heated by the ceramic heater 100.

In addition, the outer terminal member 50 is formed from a stainless steel sheet and includes an outward fitting portion 50p whose cross section in the direction orthogonal to the axial line AX has a substantially C-shape, a separator insertion portion 50s extending from near the center at the rear end side of the outward fitting portion 50p to the rear end side, and a connector portion 50c located at the further rear end side. Among them, the connector portion 50c grips the core wire of the sensor output lead wire 45 by crimping to electrically connect the outer terminal member 50 and the sensor output lead wire 45.

In addition, the separator insertion portion 50s is inserted into the separator 43, and a separator abutment portion 50d branched and protruding from the separator insertion portion 50s resiliently abuts onto a holding hole 43d of the separator 43. In this manner, the outer terminal member 50 itself is held inside the separator 43. In addition, the outward fitting portion 50p is in contact with the outer electrode 23 of the detecting element 20. Accordingly, the outer electrode 23 and the outer terminal member 50 are electrically connected to each other.

In addition, the inner terminal member 32 (corresponding to the contact terminal member) is formed from a stainless steel sheet and includes an element insertion portion 32k whose cross section in the direction orthogonal to the axial line AX has a substantially horseshoe shape, a separator insertion portion 32s extending from near the center at the rear end side of the element insertion portion 32k to the rear end side, and a connector portion 32c located at the further rear end side. Among them, the connector portion 32c grips the core wire of the sensor output lead wire 44 by crimping to electrically connect the inner terminal member 32 and the sensor output lead wire 44.

In addition, the separator insertion portion 32s is inserted into the separator 43, and a separator abutment portion 32d branched and protruding from the separator insertion portion 32s resiliently abuts onto the holding hole 43d. In this manner, the inner terminal member 32 itself is held inside the separator 43.

In addition, the element insertion portion 32k of the inner terminal member 32 is inserted into the detecting element 20 and is in contact with the inner electrode 21. Accordingly, the inner electrode 21 and the inner terminal member 32 are electrically connected to each other.

The inner terminal member 32 has a negative potential relative to the electrode pad 121. In addition, the inner terminal member 32 is in contact with the ceramic base body 102 at a position of the front end side X1 in the axial direction (lower side in FIG. 1) apart from the pad front end edge 121d (refer to FIG. 1). Specifically, by gripping the ceramic base body 102, the element insertion portion 32k of the inner terminal member 32 is in contact with the ceramic base body 102.

In this gas sensor 30, if a predetermined voltage is applied to between the outer electrode 23 and the inner electrode 21, a current flows according to a concentration difference between oxygen concentration in the exhaust gas (measured gas) in contact with the outer electrode 23 and the oxygen concentration in the air in contact with the inner electrode 21. If the current value is detected, it is possible to determine the oxygen concentration in the exhaust gas.

Conventionally, in a case where the brazing material portion is arranged up to the front end edge 121d of the electrode pad 121, moisture in the air is deposited onto the brazing material portion and the surface of the ceramic base body. This may lead to migration in which metals included in the brazing material move from the brazing material portion to the inner terminal member 32 (specifically, the element insertion portion 32k in contact with the ceramic base body), on the surface of the ceramic base body. Consequently a short circuit may arise between the brazing material portion and the contact terminal member. In particular, when using a brazing material containing Ag, migration is likely to occur between the brazing material portion and the element insertion portion 32k of the inner terminal member 32.

Figure 4:
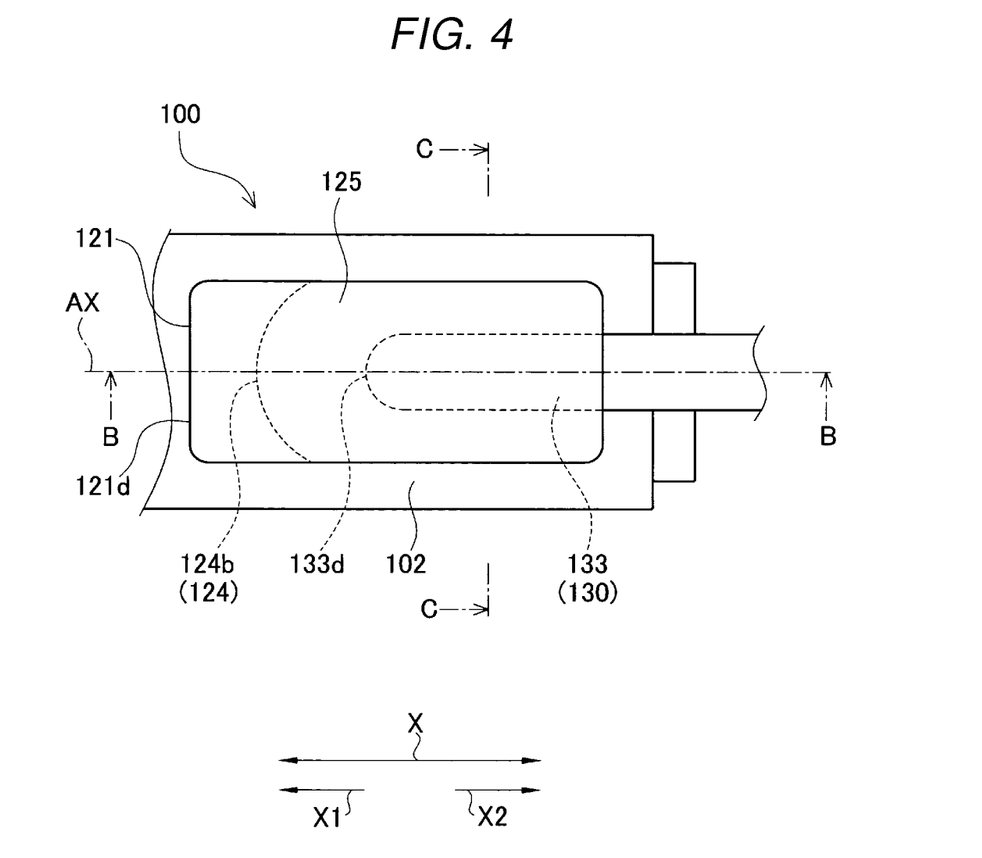
FIG. 4 is an enlarged plan view of a portion including an electrode pad within the ceramic heater.

In contrast, in the present embodiment, a brazing material front end edge 124b (front end edge of the brazing material portion 124) configuring an edge at the front end side X1 (left side in FIGS. 4 and 7) in the axial direction within the brazing material portion 124 has a convex and circular-arc shape at the front end side X1 in the axial direction and is separated from the pad front end edge 121d to the base end side X2 in the axial direction (right side in FIGS. 4 and 7).

In this manner, if the brazing material front end edge 124b of the brazing material portion 124 containing Ag is separated from the pad front end edge 121d, Ag migration is unlikely to occur between the brazing material portion 124 and the element insertion portion 32k of the inner terminal member 32.

Incidentally, within the pad front end edge 121d, an electric field is likely to concentrate on the first corner portion 121g and the second corner portion 121h. Accordingly, in particular, Ag migration is likely to occur in the first corner portion 121g and the second corner portion 121h. Therefore, the brazing material 124A containing Ag is preferably separated from the first corner portion 121g and the second corner portion 121h to the extent possible.

In contrast, in the present embodiment, the brazing material front end edge 124b has a convex and circular-arc shape at the front end side X1 in the axial direction (refer to FIGS. 4 and 7). Accordingly, it is possible to separate the brazing material portion 124 far from the first corner portion 121g and the second corner portion 121h. Therefore, Ag migration is even less likely to occur between the brazing material portion 124 and the inner terminal member 32 (element insertion portion 32k).

In addition, in the present embodiment, the brazing material front end edge 124b (front end edge of the brazing material portion 124) is configured to reach the first pad side edge 121j and the second pad side edge 121k (in other words, configured to extend from the first pad side edge 121j to the second pad side edge 121k).

Moreover, the brazing material portion 124 is arranged throughout the entire region of the electrode pad 121 at the base end side X2 in the axial direction with respect to the brazing material front end edge 124b(refer to FIGS. 4 to 7). That is, in the region of the electrode pad 121 at the base end side X2 in the axial direction (right side in FIGS. 4, 6 and 7) with respect to the brazing material front end edge 124b, the brazing material portion 124 reaches the first pad side edge 121j, the second pad side edge 121k and a pad base end edge 121m. Accordingly, it is possible to increase the bonding strength between the electrode pad 121 and the terminal connection portion 133. The pad base end edge 121m is located at the base end side but not at the first pad side edge 121j and the second pad side edge 121k, and is an edge connecting the base end of the first pad side edge 121j and the base end of the second pad side edge 121k.

In addition, in the present embodiment, in a bonding process (described below), in a state where the terminal connection portion 133 with a plate shape is arranged in the center between the first pad side edge 121j and the second pad side edge 121k, on the electrode pad 121, the melted brazing material 124A is brought into contact with the electrode pad 121 and the terminal connection portion 133 so as to infiltrate between the electrode pad 121 and the terminal connection portion 133. Consequently, the melted brazing material 124A is wetly spread on the electrode pad 121, whereby the electrode pad 121 and the terminal connection portion 133 are bonded by means of the brazing material 124A.

As described above, when bonding (brazing) the terminal connection portion 133 to the electrode pad 121 using the brazing material 124A, a portion of the melted brazing material 124A is wetly spread from the front end of the terminal connection portion 133 to the front end side X1 in the axial direction. In this regard, the distance of wet spreading is determined depending on a plate thickness T of the terminal connection portion 133.

Based on test results (described below), the distance of wet spreading of the brazing material from the front end of the terminal connection portion 133 to the front end side X1 in the axial direction is found to be approximately 6.6 times the plate thickness T of the terminal connection portion 133. Therefore, if the terminal connection portion 133 is arranged to be spaced with a distance longer than 6.6 times the plate thickness T of the terminal connection portion 133 from the pad front end edge 121d to the base end side X2 in the axial direction, it is possible to inhibit the brazing material 124A (brazing material portion 124) from being wetly spread up to the pad front end edge 121d (i.e., inhibited from reaching the pad front end edge 121d).

For this reason, in the bonding process of the present embodiment, in a state where the terminal connection portion 133 is arranged to be spaced with distance E longer than 6.6 times the plate thickness T of the terminal connection portion 133 from the pad front end edge 121d to the base end side X2 in the axial direction, the electrode pad 121 and the terminal connection portion 133 are bonded together using the brazing material 124A in the above-described manner. Accordingly, after the bonding process, it is possible to reliably separate the front end edge of the brazing material portion 124 (brazing material front end edge 124b) from the pad front end edge 121d.

In addition, the terminal connection portion 133 of the present embodiment forms a plate shape extending in the axial direction with constant width dimension W. Moreover, the front end edge of the terminal connection portion 133 (terminal front end edge 133d) is configured to have the convex shape at the front end side X1 in the axial direction (left side in FIGS. 4 and 7), and to have a circular-arc shape having a radius R from 0.5 times to 0.8 times the width dimension W (refer to FIGS. 4 and 7). In the present embodiment, it is set to the width dimension W=1.0 mm.

If the terminal front end edge 133d has the above-described shape, when bonding the electrode pad 121 and the terminal connection portion 133 together using the brazing material 124A as described above, the brazing material 124A is wetly spread substantially uniformly to the left and right (substantially vertically uniform in FIGS. 4 and 7) from the terminal front end edge 133d to the front end side X1 in the axial direction (left side in FIGS. 4 and 7). That is, it is possible to have the same degree of wet spreading of the brazing material 124A at both the first pad side edge 121j side of the electrode pad 121 and the second pad side edge 121k side.

In this manner, it is possible to prevent the brazing material 124A from reaching the front end edge 121d of the electrode pad 121 at one side due to a degree of wet spreading at one side that is larger than that in the other side between the first par side edge 121j side and the second pad side edge 121k side. Accordingly, after the bonding process, it is possible to reliably separate the front end edge of the brazing material portion 124 (brazing material front end edge 124b) from the pad front end edge 121d. That is, whereas the brazing material portion 124 has a form spreading to the front end side X1 in the axial direction rather than the terminal connection portion 133, the form of the brazing material front end edge 124b is separated from the pad front end edge 121d to the base end side X2 in the axial direction.

Next, a method of manufacturing the gas sensor 30 according to the present embodiment will be described.

First, the ceramic heater 100 is manufactured. Specifically, as illustrated in FIG. 3, a green sheet 140 made of alumina ceramic is provided in which the heater element 141 and the electrode pad 121 are formed. Further, a green sheet 146 made of alumina ceramic is provided. Then, the green sheet 146 is pressed against the green sheet 140, and these are wound around the porcelain tube 101 to form a ceramic heater molded body. Thereafter, the ceramic base body 102 is obtained by firing the ceramic heater molded body.

Next, after preparing the heater terminal member 130, in a subsequent bonding process, the electrode pad 121 located on the surface of the ceramic base body 102 and the terminal connection portion 133 of the heater terminal member 130 are bonded together using the brazing material 124A. More specifically, as illustrated in FIG. 7, the terminal connection portion 133 is arranged in the center between the first pad side edge 121j and the second pad side edge 121k, on the electrode pad 121, and is arranged at a position spaced with a distance E longer than 6.6 times the plate thickness T (refer to FIG. 5) of the terminal connection portion 133 from the pad front end edge 121d to the base end side X2 in the axial direction.

Next, in a state where the brazing material 124A is arranged at the position in contact with the electrode pad 121 and the terminal connection portion 133, the brazing material 124A is melted by heating. In this manner, the melted brazing material 124A is brought into contact with the electrode pad 121 and the terminal connection portion 133 to infiltrate between the electrode pad 121 and the terminal connection portion 133 and to wetly spread on the electrode pad 121. Thereafter, if the brazing material 124A is cooled down, the brazing material portion 124 is formed and the heater terminal member 130 (terminal connection portion 133) is bonded to the electrode pad 121. In this manner, the ceramic heater 100 illustrated in FIG. 2 is completed.

According to the present embodiment, in the bonding process, the melted brazing material 124A is not wetly spread up to the front end edge 121d of the electrode pad 121 (i.e., the melted brazing material 124A does not reach the pad front end edge 121d). The reason is that the terminal connection portion 133 is arranged to be spaced with a distance E longer than 6.6 times the plate thickness T of the terminal connection portion from the pad front end edge 121d to the base end side X2 in the axial direction. Therefore, the brazing material portion 124 can be separated from the front end edge 121d of the electrode pad 121.

Figure 8:
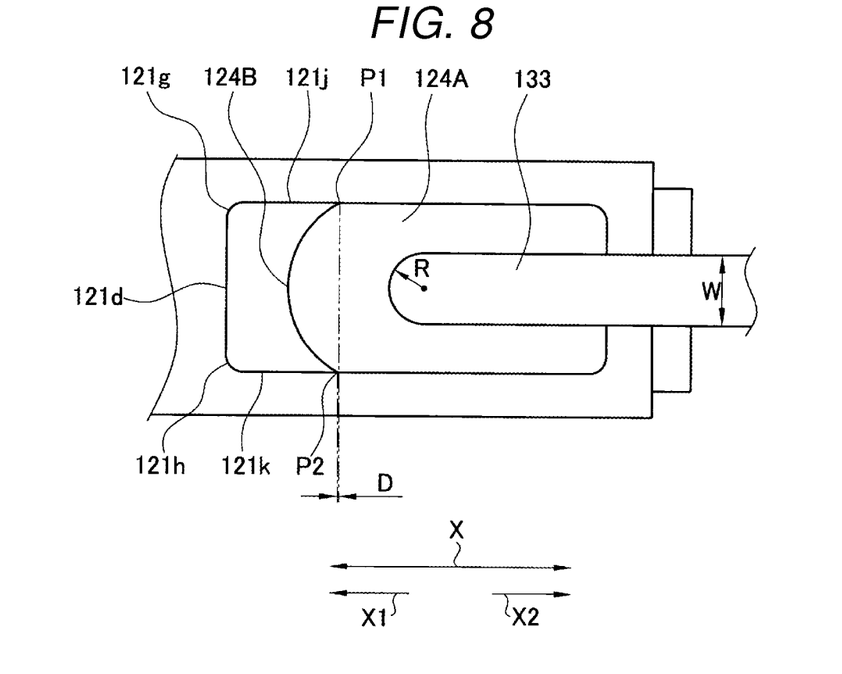
FIG. 8 is a plan view illustrating a wetly spreading form of the brazing material according to an embodiment of the invention.

Moreover, in the present embodiment, the front end edge of the terminal connection portion 133 (terminal front end edge 133d) has a convex shape at the front end side X1 in the axial direction (left side in FIG. 7) and has a circular-arc shape having a radius R from 0.5 times to 0.8 times the width dimension W (refer to FIGS. 7 and 8). Accordingly, in the bonding process, the brazing material 124A is wetly spread substantially uniformly to the left and right (vertically in FIG. 7) from the terminal front end edge 133d to the front end side X1 in the axial direction (left side in FIG. 7). That is, it is possible to have the same degree of wet spreading of the brazing material 124A at both the first pad side edge 121j side of the electrode pad 121 and the second pad side edge 121k side.

Therefore, it is possible to prevent the brazing material 124A from reaching the front end edge 121d of the electrode pad 121 at one side due to a degree of wet spreading in one side is larger than that at the other side between the first pad side edge 121j side and the second pad side edge 121k side. Accordingly, after the bonding process, it is possible to reliably separate the brazing material front end edge 124b and the pad front end edge 121d. That is, the brazing material portion 124 does not reach the pad front end edge 121d and can have a form spreading to the front end side X1 in the axial direction rather than the terminal connection portion 133.

Furthermore, the brazing material front end edge 124b can have the convex and circular-arc shape at the front end side X1 in the axial direction (refer to FIG. 7). Accordingly, the brazing material portion 124 can be separated far from the first corner portion 121g and the second corner portion 121h.

Thereafter, in an assembly process, using a known assembly method (for example, refer to JP-A-2004-053425), the ceramic heater 100, the detecting element 20, the metallic shell 31, outer terminal member 50 and the inner terminal member 32 which are manufactured as described above are assembled. Accordingly, the gas sensor 30 illustrated in FIG. 1 is completed.

<Front End Edge Shape of Terminal Connection Portion>

In the bonding process, the form in which the melted brazing material is wetly spread to the front end side on the electrode pad is considered to differ depending on the shape of the front end edge (terminal front end edge) of the terminal connection portion. In particular, if the brazing material can be wetly spread substantially uniformly to the left and right from the terminal front end edge to the front end side in the axial direction, it is possible to inhibit the brazing material from being wetly spread up to the front end edge of the electrode pad (i.e., to inhibit the brazing material from reaching the pad front end edge). Conversely, if the degree of the wet spreading at one side is larger than at the other side between the first pad side edge side and the second pad side edge side of the electrode pad, the brazing material is considered to likely reach the front end edge of the electrode pad at one side. Therefore, preferred shapes of the terminal front end edge were investigated.

Specifically, terminal connection portions (samples A to F) having different terminal front end edge shapes were prepared as follows and wetly spreading examples of the brazing material 124A in the bonding process were investigated.

Figure 9:
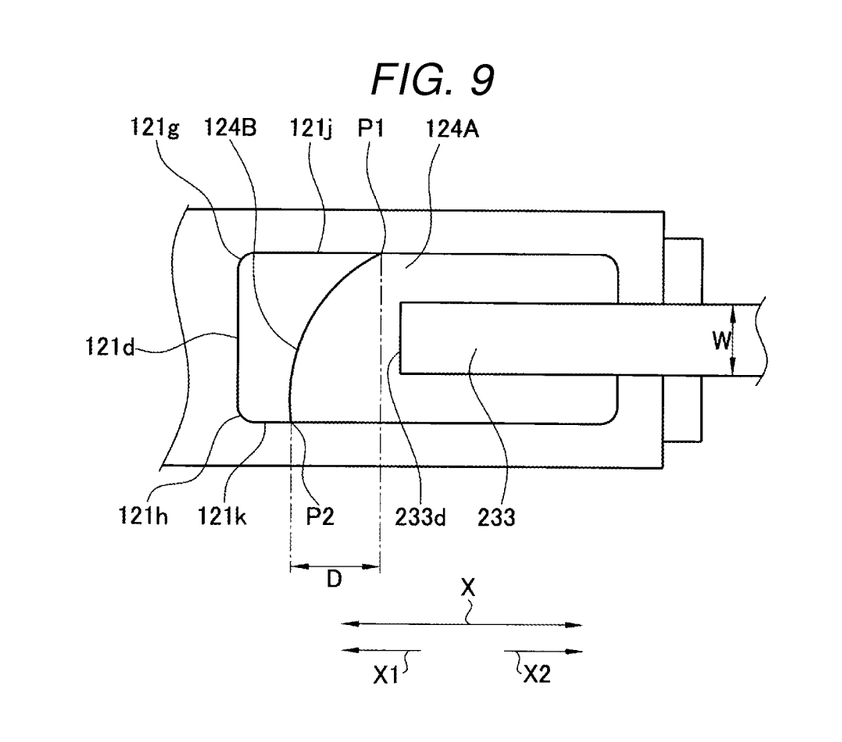
FIG. 9 is a plan view illustrating a wetly spreading form of a brazing material according to a comparative example.

As illustrated in FIG. 9, sample A (comparative example) had a flat plate shape extending in the direction of the axial line X with constant width dimension W and is a terminal connection portion 233 where the terminal front end edge 233d has a linear shape. In addition, samples B to F had a flat plate shape extending in the axial direction with constant width dimension W, and are common in that the terminal connection portion had the terminal front end edge with a convex and circular-arc shape at the front end side in the axial direction. However, the radii R of the circular-arc shape in the terminal front end edge were individually different.

Specifically, the terminal front end edge of sample B had a radius R of 0.9 times the width dimension W. In addition, the terminal front end edge of sample C had a radius R of 0.8 times the width dimension W. In addition, the terminal front end edge of sample D had a radius R of 0.7 times the width dimension W. In addition, the terminal front end edge of the sample E had a radius R of 0.6 times the width dimension W. In addition, the terminal front end edge of the sample F had a radius R of 0.5 times the width dimension W. The width dimension W of all Samples was 1.0 mm Samples A and B are comparative examples and samples C to F are embodiments of the invention.

The results are shown in Table 1. As illustrated in FIG. 8, in Table 1, "O" represents a case where the brazing material 124A was wetly spread substantially uniformly to the left and right from the terminal front end edge to front end side X1 in the axial direction. On the other hand, as illustrated in FIG. 9, "X" represents a case where the degree of wet spreading at one side (in the example of FIG. 9, the second pad side edge 121k side) was larger than at the other side between the first pad side edge 121j side and the second pad side edge 121k side of the electrode pad 121.

Specifically, as illustrated in FIGS. 8 and 9, the brazing material 124A was determined to have been wetly spread substantially uniformly to the left and right (as "O") in a case where a position where the front end edge 124B of the brazing material 124A came into contact with the first pad side edge 121j (referred to as a first contact point P1) and a position where the front end edge 124B of the brazing material 124A came into contact with the second pad side edge 121k (referred to as a second contact point P2) were detected. Further, a positional difference D in the axial direction between the first contact point P1 and the second contact point P2 was less than a threshold value Th. In a case where the positional difference D was equal to or more than the threshold value Th, the degree of wet spreading at one side was determined to be larger than in the other side (as "X").

The threshold value Th was set to half (that is, 1.0 mm/2=0 5 mm) the width dimensions W of the terminal connection portion 133.

TABLE 1

|  | Shape of Terminal Front End Edge | Wet Spreading Form of Brazing Material |
|---|---|---|
| Sample A | Linear Shape | X |
| Sample B | Circular-Arc Shape with R = 0.9W | X |
| Sample C | Circular-Arc Shape with R = 0.8W | O |

TABLE 1-continued

|  | Shape of Terminal Front End Edge | Wet Spreading Form of Brazing Material |
|---|---|---|
| Sample D | Circular-Arc Shape with R = 0.7W | ◯ |
| Sample E | Circular-Arc Shape with R = 0.6W | ◯ |
| Sample F | Circular-Arc Shape with R = 0.5W | ◯ |

Based on the results illustrated in Table 1, the front end edge of the terminal connection portion (terminal front end edge) preferably has a convex shape at the front end side in the axial direction and has a circular-arc shape with a radius R from 0.5 times to 0.8 times the width dimension W. If the terminal front end edge has such a shape, in the bonding process, the brazing material 124A can be wetly spread substantially uniformly to the left and right (vertically in FIG. 8) from the terminal front end edge to the front end side X1 in the axial direction (left side in FIG. 8). That is, it is possible to have the same degree of wet spreading of the brazing material 124A at both the first pad side edge 121j side of the electrode pad 121 and the second pad side edge 121k side.

Incidentally, within the pad front end edge 121d, the electric field is likely to concentrate on the first corner portion 121g and the second corner portion 121h. Accordingly, in particular, Ag migration is likely to occur at the first corner portion 121g and the second corner portion 121h. Therefore, the brazing material 124A containing Ag is preferably separated from the first corner portion 121g and the second corner portion 121h as far as possible. Further in this regard, the brazing material is preferably wetly spread substantially uniformly to the left and right from the terminal front end edge to the front end side in the axial direction.

Specifically, as illustrated in FIG. 8, in a case where the brazing material 124A has been wetly spread substantially uniformly to the left and right from the terminal front end edge to the front end side in the axial direction, it is possible to separate the front end edge 124B of the brazing material 124A far from the first corner portion 121g and the second corner portion 121h. On the other hand, as illustrated in FIG. 9, in a case where the degree of wet spreading at one side (in the example of FIG. 9, the second pad side edge 121k side) is larger than at the other side between the first pad side edge 121j side and the second pad side edge 121k side of the electrode pad 121, the front end edge 124B of the brazing material 124A comes close to one side corner portion (in the example of FIG. 9, the second corner portion 121h).

In this evaluation, each of the samples was arranged to be spaced with distance longer than 6.6 times (e.g., 10 times) the plate thickness of the terminal connection portion from the pad front end edge to base end side in the axial direction. Therefore, in the samples, the brazing material 124A was not wetly spread up to the front end edge 121d of the electrode pad 121 (i.e., did not reach the pad front end edge 121d).

<Wetly Spreading of Brazing Material>

In the bonding process according to the present embodiment, when bonding the electrode pad 121 and the terminal connection portion 133 together using the brazing material 124A, a portion of the melted brazing material 124A is wetly spread from the front end of the terminal connection portion 133 to the front end side X1 in the axial direction, on the electrode pad 121. However, the spreading distance is considered to vary depending on the plate thickness of the terminal connection portion 133. Thus, the distance where the brazing material 124A is wetly spread on the electrode pad 121 by setting a constant plate thickness (0.3 mm) of the terminal connection portion 133 and by changing the distance E in the direction of the axial line from the pad front end edge 121d to the terminal connection portion 133 was investigated.

Specifically, whether or not the brazing material 124A is wetly spread up to (i.e., so as to reach) the pad front end edge 121d in the bonding process was investigated, by changing the distance E in the axial direction (refer to FIG. 7) from the pad front end edge 121d to the terminal connection portion 133 within a range of from 0.6 mm to 4.6 mm. The results are shown in Table 2. In Table 2, "X" represents a case where the brazing material 124A was wetly spread up to (i.e., so as to reach) the pad front end edge 121d, and "◯" represents a case where the brazing material 124A was not wetly spread up to (i.e., did not reach) the pad front end edge 121d.

TABLE 2

|  | Distance E (mm) | Wetly Spreading of Brazing Material |
|---|---|---|
| Sample 1 | 0.6 | X |
| Sample 2 | 1.0 | X |
| Sample 3 | 1.4 | X |
| Sample 4 | 1.8 | X |
| Sample 5 | 2.0 | ◯ |
| Sample 6 | 2.2 | ◯ |
| Sample 7 | 2.6 | ◯ |
| Sample 8 | 3.0 | ◯ |
| Sample 9 | 3.4 | ◯ |
| Sample 10 | 3.6 | ◯ |
| Sample 11 | 4.0 | ◯ |
| Sample 12 | 4.2 | ◯ |
| Sample 13 | 4.4 | ◯ |
| Sample 14 | 4.6 | ◯ |

As illustrated in FIG. 2, in the case where the distance E in the direction of the axial line was set to 1.8 mm or less, the brazing material 124A had wetly spread up to (i.e., had reached) the pad front end edge 121d. On the other hand, in the case where the distance E in the axial direction was set to 2.0 mm or more, the brazing material 124A had not wetly spread up to (i.e., had not reached) the pad front end edge 121d. These results reveal that the distance where the brazing material 124A is wetly spread from the front end of the terminal connection portion 133 to the front end side X1 in the axial direction is approximately 6.6 times the plate thickness of the terminal connection portion 133. The plate thickness of the terminal connection portion 133 is 0.3 mm.

Based on the above results, if the terminal connection portion is arranged to be spaced with a distance longer than 6.6 times the plate thickness of the terminal connection portion from the pad front end edge to the base end side in the axial direction, it is possible to reliably prevent the brazing material (brazing material portion) from being wetly spread up to the front end edge of the electrode pad (from reaching the pad front end edge).

The invention has been described in detail with reference to the above embodiments. However, the invention should not be construed as being limited thereto. It should further be apparent to those skilled in the art that various changes in form and detail of the invention as shown and described above may be made. It is intended that such changes be included within the spirit and scope of the claims appended hereto.

This application is based on Japanese Patent Application No. 2012-132510 filed Jun. 12, 2012, incorporated herein by reference in its entirety.

What is claimed is:

1. A gas sensor having an axis, a rear end side and a front end side, the gas sensor including a ceramic heater and a contact terminal member, the ceramic heater comprising:

a ceramic base body having a bar shape extending in the axial direction and a heater element disposed inside the ceramic base body;

an electrode pad disposed on a surface of a base end side in the axial direction of the ceramic base body and conductive with the heater element, the electrode pad having a first pad side edge and a second pad side edge extending parallel to the axial direction, and a pad front end edge located at a front end side in the axial direction with respect to the first and second pad side edges and connecting a front end of the first pad side edge and a front end of the second pad side edge;

a heater terminal member having a terminal connection portion arranged at the base end side in the axial direction apart from the pad front end edge; and a brazing material portion formed of a brazing material containing Ag, arranged on the electrode pad and interposed between the electrode pad and the terminal connection portion to bond the electrode pad and the terminal connection portion, and the contact terminal member having a negative potential relative to the electrode pad and coming into contact with the ceramic base body at the front end side in the axial direction apart from the pad front end edge, wherein the terminal connection portion has a plate shape extending in the axial direction having a constant width dimension, and a terminal front end edge thereof has a convex shape at the front end side in the axial direction and has a circular-arc shape with a radius from 0.5 times to 0.8 times the width dimension, which terminal connection portion is arranged in the center between the first pad side edge and the second pad side edge, on the electrode pad, wherein the brazing material portion has a form spreading to the front end side in the axial direction away from the terminal connection portion, and wherein a brazing material front end edge which is a front end edge of the brazing material portion has a convex and circular-arc shape at the front end side in the axial direction, and configured to be apart from the pad front end edge.

2. The gas sensor as claimed in claim 1,
wherein the terminal connection portion is arranged on the electrode pad, at a position spaced with a distance longer than 6.6 times the plate thickness of the terminal connection portion from the pad front end edge to the base end side in the axial direction.

3. The gas sensor as claimed in claim 1, further comprising:
a plated layer covering the brazing material portion and formed of a metal selected from the group consisting of nickel, chromium and gold.

4. A ceramic heater having an axis, a rear end side and a front end side, the ceramic heater comprising:

a ceramic base body having a bar shape extending in the axial direction and a heater element disposed inside the ceramic base body;

an electrode pad disposed on a surface of a base end side in the axial direction of the ceramic base body and conductive with the heater element, the electrode pad having a first pad side edge and a second pad side edge extending parallel to the axial direction, and a pad front end edge located at a front end side in the axial direction with respect to the first and second pad edges and connecting a front end of the first pad side edge and a front end of the second pad side edge;

a heater terminal member having a terminal connection portion arranged at the base end side in the axial direction apart from the pad front end edge; and a brazing material portion formed of a brazing material containing Ag, arranged on the electrode pad and interposed between the electrode pad and the terminal connection portion to bond the electrode pad and the terminal connection portion, wherein the terminal connection portion has a plate shape extending in the axial direction having a constant width dimension, and a terminal front end edge thereof has a convex shape at the front end side in the axial direction and has a circular-arc shape with a radius from 0.5 times to 0.8 times the width dimension, which terminal connection portion is arranged in the center between the first pad side edge and the second pad side edge, on the electrode pad, wherein the brazing material portion has a form spreading to the front end side in the axial direction away from the terminal connection portion, and wherein a brazing material front end edge which is a front end edge of the brazing material portion has a convex and circular-arc shape at the front end side in the axial direction, and configured to be apart from the pad front end edge.

5. The ceramic heater as claimed in claim 4,
wherein the terminal connection portion is arranged on the electrode pad, at a position spaced with a distance longer than 6.6 times the plate thickness of the terminal connection portion from the pad front end edge to the base end side in the axial direction.

6. The ceramic heater as claimed in claim 4, further comprising:
a plated layer covering the brazing material portion and formed of a metal selected from the group consisting of nickel, chromium and gold.

* * * * *